US00PP08320P

United States Patent [19]

Kamemoto et al.

[11] Patent Number: Plant 8,320

[45] Date of Patent: Jul. 27, 1993

[54] ANTHURIUM CULTIVAR NAMED KALAPANA

[75] Inventors: Haruyuki Kamemoto; Adelheid R. Kuehnle, both of Honolulu, Hi.

[73] Assignee: University of Hawaii, Honolulu, Hi.

[21] Appl. No.: 708,852

[22] Filed: May 31, 1991

[51] Int. Cl.[5] ..... A01H 5/00

[52] U.S. Cl. ..... Plt./88.1

[58] Field of Search ..... Plt./88, 88.1

[56] References Cited

U.S. PATENT DOCUMENTS

| | | | |
|---|---|---|---|
| P.P. 4,375 | 2/1979 | Holtkamp | Plt. 88.1 |
| P.P. 4,376 | 2/1979 | Holtkamp | Plt. 88.1 |
| P.P. 5,696 | 3/1986 | Laarse | Plt. 88.1 |
| P.P. 6,235 | 7/1988 | Arndt | Plt. 88.1 |
| P.P. 7,044 | 10/1989 | Hayashi | Plt. 88.1 |
| P.P. 7,441 | 2/1991 | Tagami | Plt. 88.1 |

OTHER PUBLICATIONS

Kamemoto, H. et al., "Diamond Jubilee Anthurium," U. of Hawaii Hort. Digest 65:4–5 (1982).

Kamemoto, H. et al., "Paradise Pink Anthurium," U. of Hawaii Hort. Digest 62:5 (1981).

Kamemoto, H. et al., "Breeding for Blight Resistance: A Progress Report," Anthurium Blight Conference Proceedings, Feb. 22–24, 1989, p. 10 (1989).

*Primary Examiner*—James R. Feyrer

*Attorney, Agent, or Firm*—James C. Weseman

[57] ABSTRACT

A new and distinct anthurium cultivar named Kalapana is characterized by its red-green, broad heart-shaped spathe carried above the foliage on a long, erect peduncle. The slightly reclining spadix is yellow to orange, turning white with maturity. Kalapana is resistant to anthracnose (spadix rot) and is tolerant to the systemic phase of bacterial blight.

1 Drawing Sheet

TECHNICAL FIELD

The present invention comprises a new and distinct cultivar of Anthurium, botanically known as *Anthurium andraeanum*, and hereinafter referred to by the cultivar name Kalapana.

DISCOVERY OF THE NEW CULTIVAR

The new cultivar is a product of the planned anthurium breeding program of the University of Hawaii, Honolulu, Hi. Kalapana was discovered and selected on Apr. 10, 1983 from a cross made on Sep. 1, 1980 between cultivars developed earlier by the University of Hawaii: Diamond Jubilee (female parent) and Paradise Pink (pollen parent). Subsequent asexual reproduction and evaluation revealed the combination of a number of desirable horticultural characteristics, especially the red obake spathe, resistance of the spadix to anthracnose (caused by *Colletotrichum gloeosporioides*), and tolerance to the bacterial blight (caused by *Xanthomonas campestris* pv. dieffenbachiae). This combination of characteristics has demonstrated stability from generation to generation.

The following traits have been repeatedly observed and distinguish Kalapana as a new and distinct cultivar from other Anthurium of the same general type:

1. The red obake spathe ranges from 14 cm to 24 cm (median approximately 18 cm) in length and 16 cm to 21 cm (median approximately 18 cm) in width, with slightly overlapping lobes. It is light red (45 C Royal Horticultural Society Colour Chart) with green (143B R.H.S.C.C.) restricted to the lobes, but sometimes extending toward the tip. It is carried at an angle of approximately 70 to 90 degrees from the peduncle (flower stem).

2. The spadix ranges from 5.7 cm to 7.3 cm (median approximately 7 cm) in length, 8 mm to 16 mm (median approximately 12 mm) in diameter, slightly recurved, yellow-orange (22A R.H.S.C.C.) to organce-red (31A R.H.S.C.C.), turning white with maturity and is resistant to anthracnose.

3. The peduncle is long and erect, and carries the spathe well above the foliage.

4. The leaf blade ranges from 28 cm to 38 cm (median approximately 33 cm) in length, 15 cm to 19 cm (median approximately 17 cm) in width and is heart-shaped.

5. The plant is tolerant to the systemic phase of the bacterial blight.

All color references are measured against the Royal Horticultural Society Colour Chart (R.H.S.C.C.), The Royal Horticultural Society, London, England, except where general color terms of ordinary significance are employed. The color references are approximate, as color depends to a degree on horticultural practices such as light level and degree of fertilization, among others.

ASEXUAL REPRODUCTION

Plants were asexually reproduced by separation of suckers and by taking top cuttings. Also the tissue culture method has been used to multiply this cultivar. All propagations that flowered have been true to the original type in plant and flower characteristics.

BRIEF DESCRIPTION OF THE DRAWINGS

The new cultivar is illustrated by the accompanying color photographic drawings in which.

Figure 1:
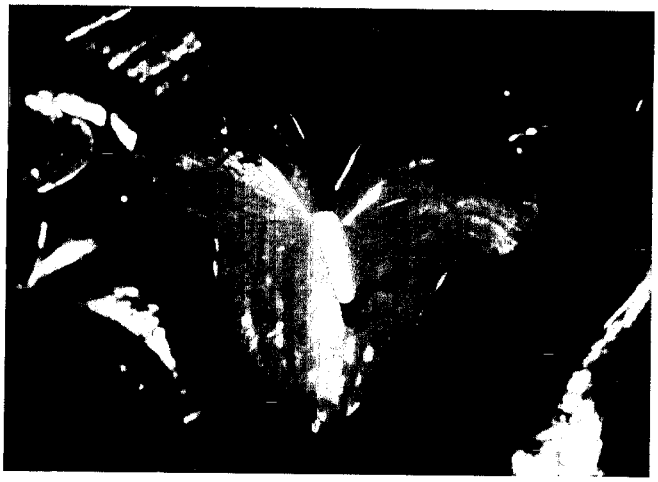
FIG. 1 is a front view which shows a representative flower of the new cultivar.
Figure 2:
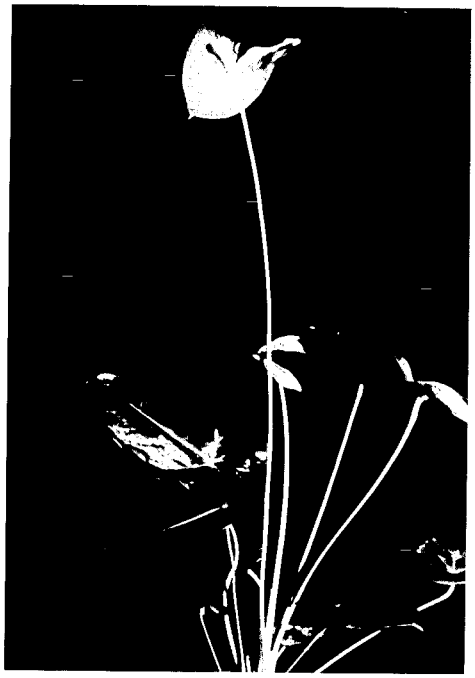
FIG. 2 is a front view which shows representative plant growth habit and carriage of a flower of the new cultivar.

The colors are as accurate as is reasonably possible with color illustrations of this type.

DESCRIPTION OF THE NEW CULTIVAR

The following observations, measurements and values describe the new cultivar grown in Honolulu, Hi. under shadehouse conditions which closely approximate those generally in use in Anthurium horticultural practice:

Origin:

*Male parent.*—Paradise Pink cultivar developed by the University of Hawaii and released in 1981.

*Female parent.*—Diamond Jubilee cultivar developed by the University of Hawaii and released in 1982.

Classification: *Anthurium andraeanum,* cv. Kalapana.

Plant: A three year old plant grown in a 3 gallon size container ranges from 88 cm to 102 cm (median approximately 92 cm) in height and 55 cm to 67 cm (median approximately 61 cm) in width. It will continue to grow taller until topped.

Leaf:

*Form*—The leaf blade is cordate with an acuminate tip (generally termed "heart-shaped"). The margins are entire.

*Size.*—Leaf blades of a mature sized plant range from 28 cm to 38 cm (median approximately 33 cm) in length and 17 cm to 19 cm (median approximately 18 cm) in width.

*Petiole.*—The petiole ranges from 45 cm to 57 cm (median approximately 51 cm) in length from the base of the petiole to the base of the leaf blade. The petiole ranges from 4 mm to 6 mm (median approximately 5 mm) in diameter immediately below the geniculum.

*Lobes.*—The leaf has two lobes extending past the petiole. The distance from the petiole/leaf juncture to the highest point on the lobes ranges from 7 cm to 9 cm (median approximately 8 cm).

*Color.*—Upper surface: green (138A R.H.S.C.C.). Lower surface: green (138D R.H.S.C.C.).

Sucker production: High

Inflorescence:

*Immature.*—The spathe is tightly rolled around the spadix and extrudes from the petiole sheath. The spathe is fully open approximately when the peduncle is fully elongated.

*Mature.*—Size — The flattened spathe ranges from 14 cm to 24 cm (median approximately 18 cm) in length and 16 cm to 21 cm (median approximately 18 cm) in width, although some spathes may attain larger size. Shape — The spathe is broadly cordate with an acuminate tip and with large lobes, slightly overlapping. Color — Upper surface: light red (45C R.H.S.C.C.) with green (143B R.H.S.C.C.) usually restricted to the lobes, but sometimes extending toward the tip. Lower surface: red (45D R.H.S.C.C.), green (143C R.H.S.C.C.). Position — The spathe is carried on a straight peduncle above the leaves at approximately 70 to 90 degrees from the peduncle.

Reproductive organs:

*Spadix.*—Size and Shape — Ranges from 5.7 cm to 7.3 cm (median approximately 7 cm) in length and 8 mm to 16 mm (median approximately 12 mm) in thickness, slightly recurved. Color — When the spathe unrolls, the spadix is yellow-orange (22A R.H.S.C.C.) to orange-red (31A R.H.S.C.C.), turning white with maturity. Stamens — Anthers and filaments are not clearly visible. Pollen — White in color.

Peduncle (flower stem): Ranges from 63 cm to 69 cm (median approximately 66 cm) in length, and 6 mm to 10 mm (median approximately 8 mm) in diameter, long and erect.

Roots: Fleshy white roots with smaller laterals.

Disease resistance: Highly resistant to anthracnose (spadix rot); tolerant to the systemic phase of the bacterial blight, in that the cultivar can become infected with *Xanthomonas campestris* pv. dieffenbachiae but the infection is usually localized and non-systemic.

General Observations

Kalapana is an attractive red-green, medium-sized obake anthurium with good vase life. It is a vigorous grower and will produce approximately six flowers per plant per year. Flowers on young plants are small and progressively get larger as plants grow. The spathe is carried on a long, straight peduncle well above the foliage. Kalapana is especially desirable because of its resistance to anthracnose (spadix rot) and tolerance to the systemic phase of bacterial blight.

Due to the unique combination of characteristics as illustrated and described, Kalapana provides an excellent new Anthurium cultivar for commercial cropping.

We claim:

1. A new and distinct *Anthurium andraeanum* cultivar substantially as described and illustrated, known by the cultivar name Kalapana and characterized by the combined features of red obake spathe with slightly overlapping lobes, yellow to orange spadix turning white with maturity, long and straight peduncle carrying the spathe at approximately 70 to 90 degrees from the peduncle and well above the foliage, heart-shaped green leaf blade, good flower yield, resistance to anthracnose (spadix rot), and tolerance to the systemic phase of bacterial blight.

* * * * *